(12) United States Patent
Al Rasheed

(10) Patent No.: US 9,173,598 B1
(45) Date of Patent: Nov. 3, 2015

(54) DEVICE FOR PIERCING THE SKIN TO OBTAIN A BLOOD SAMPLE AND METHOD OF USE

(76) Inventor: Abdullah Khalid Al Rasheed, Riyadh (SA)

(*) Notice: Subject to any disclaimer, the term of this patent is extended or adjusted under 35 U.S.C. 154(b) by 496 days.

(21) Appl. No.: 13/595,281

(22) Filed: Aug. 27, 2012

(51) Int. Cl.
*A61B 5/15* (2006.01)

(52) U.S. Cl.
CPC ..................................... *A61B 5/1411* (2013.01)

(58) Field of Classification Search
CPC .................. A61M 37/0015; A61M 2037/0023; A61M 2037/003; A61M 2037/0038; A61M 2037/0046; A61M 2037/0053; A61M 2037/0061; A61B 5/1411; A61B 5/150167; A61B 5/150282; A61B 5/150412; A61B 5/151; A61B 5/15105
See application file for complete search history.

(56) References Cited

U.S. PATENT DOCUMENTS

| | | | |
|---|---|---|---|
| 4,793,505 A * | 12/1988 | Towns .................... | B65D 55/02 215/250 |
| 6,126,037 A * | 10/2000 | Lifshey ............................. | 222/1 |
| 6,589,260 B1 * | 7/2003 | Schmelzeisen-Redeker et al. .............................. | 606/181 |
| 2003/0050602 A1 * | 3/2003 | Pettis et al. .................... | 604/117 |
| 2005/0256045 A1 * | 11/2005 | Ameri et al. ..................... | 514/12 |
| 2006/0173410 A1 * | 8/2006 | Moberg et al. ................ | 604/110 |
| 2013/0138013 A1 * | 5/2013 | Hein et al. ...................... | 600/556 |

\* cited by examiner

*Primary Examiner* — Thomas McEvoy
(74) *Attorney, Agent, or Firm* — Ted Masters

(57) ABSTRACT

A device for piercing the skin to obtain a blood sample includes a sleeve which has an open first end and a cavity. A piercer is disposed within the cavity, and has a tip which is positioned near the open first end of the sleeve. The user applies opposing finger pressure to the device so that the skin of one finger enters the cavity and is pierced by the piercer. During this operation the piercer does not move with respect to the sleeve.

6 Claims, 5 Drawing Sheets

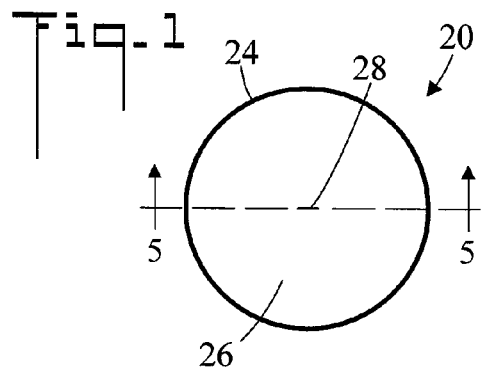
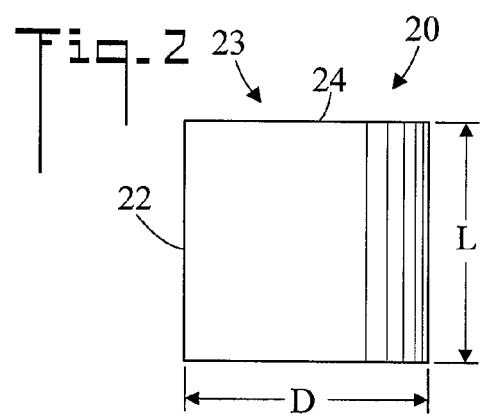
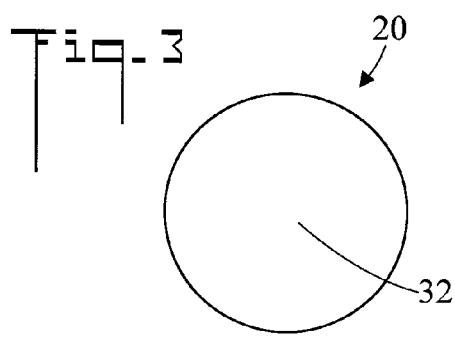
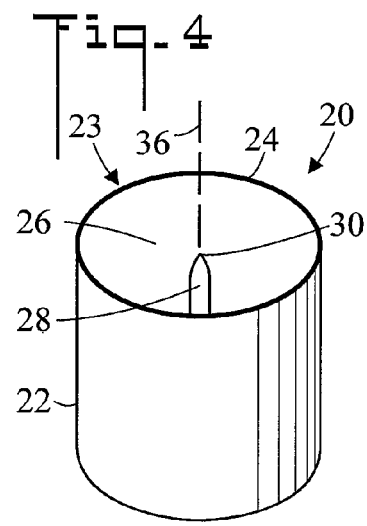
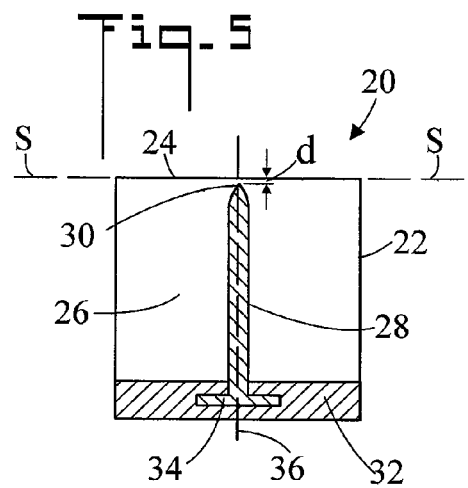

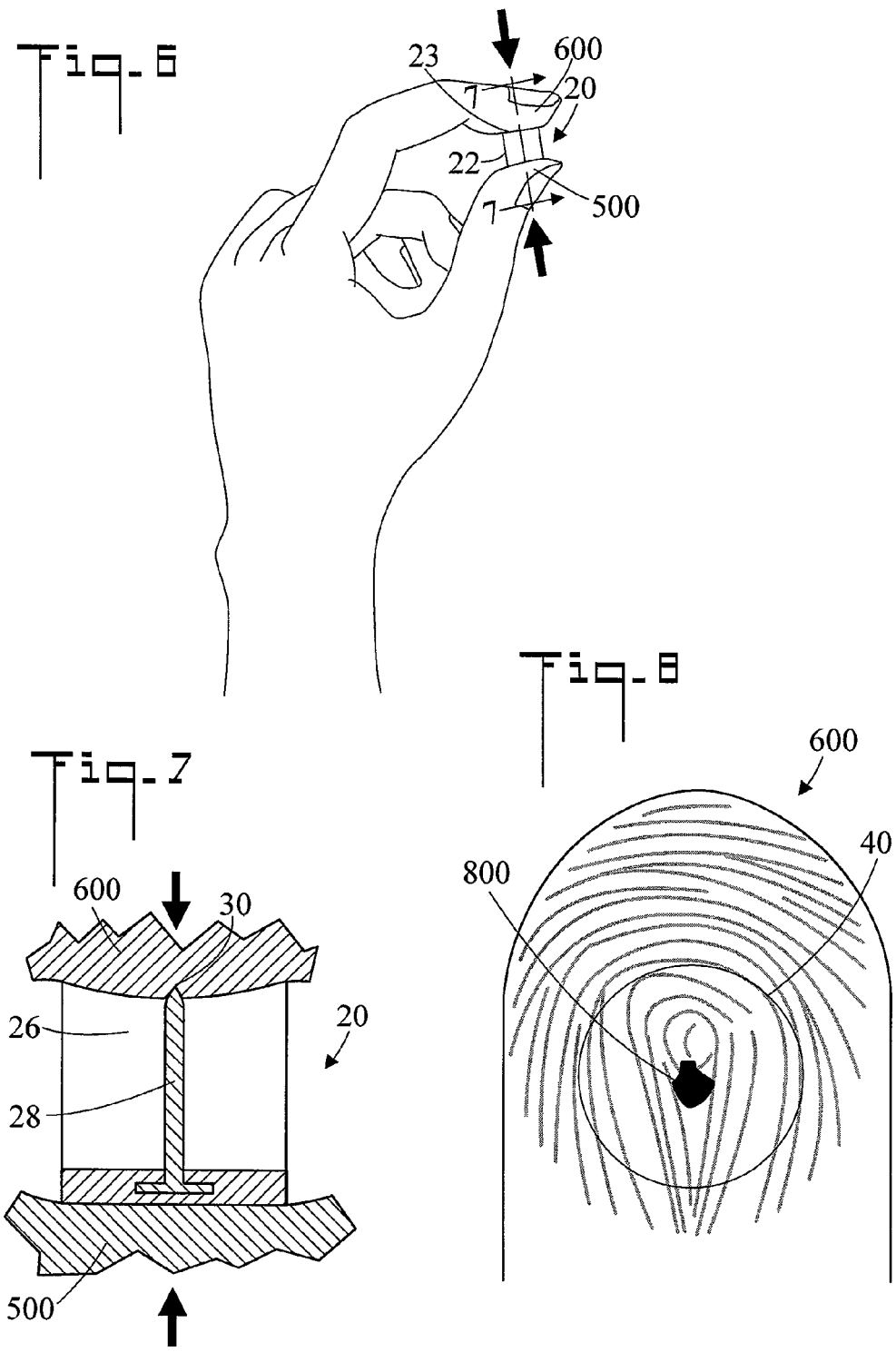

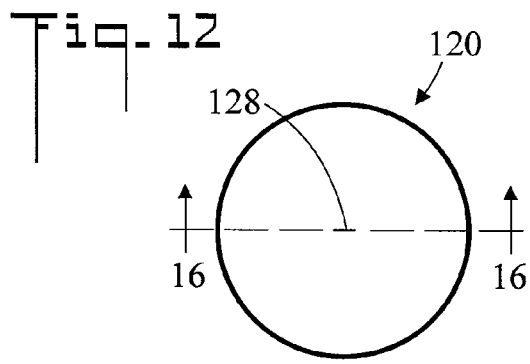
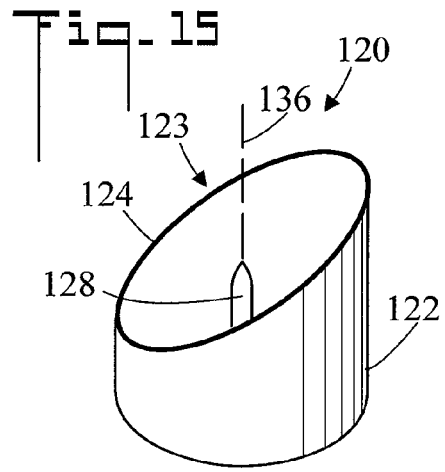
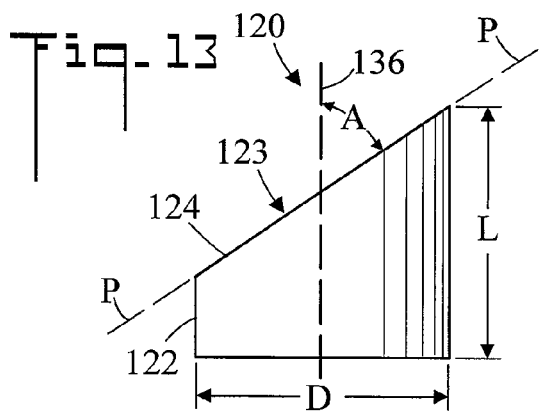
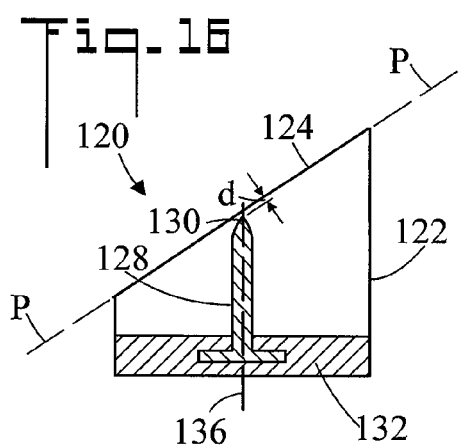
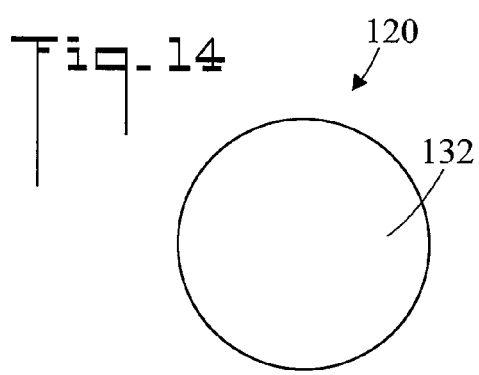

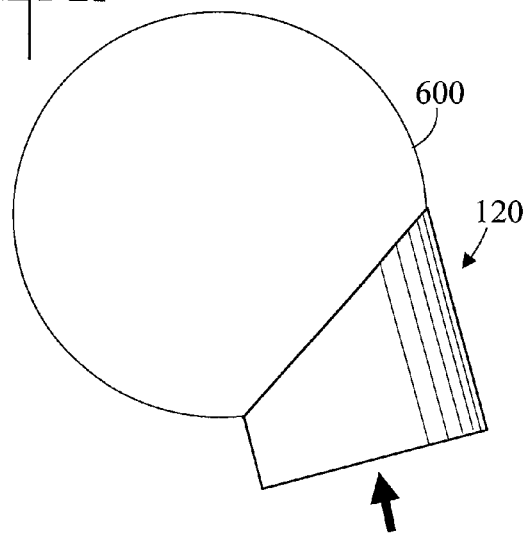
Fig_17
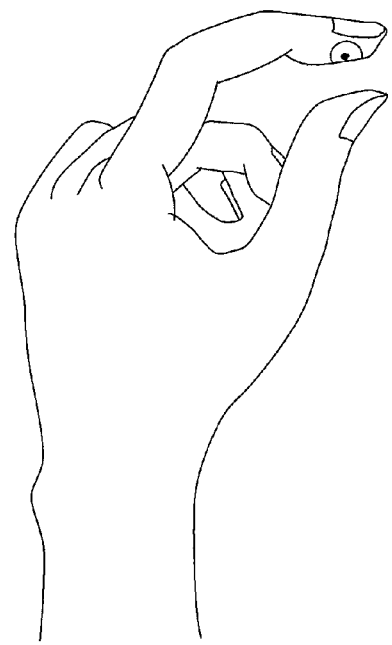
Fig_19
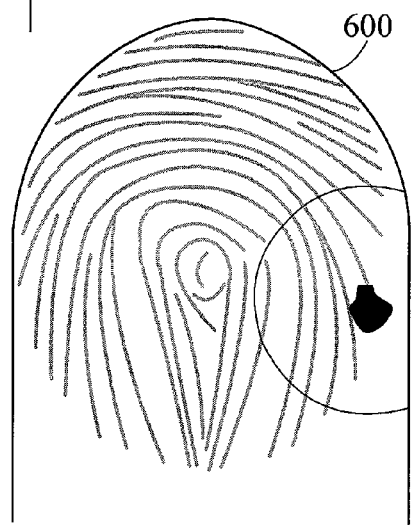
Fig_18

DEVICE FOR PIERCING THE SKIN TO OBTAIN A BLOOD SAMPLE AND METHOD OF USE

TECHNICAL FIELD

The present invention pertains generally to the field of medicine, and more particularly to a device and method for piercing the skin to obtain a blood sample.

BACKGROUND OF THE INVENTION

Disposable lancets are used to obtain a drop of blood for glucose testing of diabetic patients. The lancets should not be used for multiple patients, since such use can lead to blood borne cross infection such as hepatitis, AIDS, and the like. Recently, it have been documented even tiny dry blood clot on the device can incubate viable viruses.

There are several types of disposable lancets in the market, but unfortunately these tend to be both large in size and expensive. Some of the needles are retractable to prevent re-use and needle-stick injury. Most contain a spring which retracts the needle. Some utilize the material resilience to induce the needle retraction after puncturing the skin. Others require the use of both hands to manipulate the lancet. Moreover, all disposable lancet in the prior art use the rapid action pricking mechanism to make the skin penetration. This rapid action induces sharp pain and discomfort to the user.

BRIEF SUMMARY OF THE INVENTION

The present invention is directed to a small, disposable, single-use, device for piercing the skin to obtain a blood sample. The device is simply held between two fingers of one hand (e.g. the thumb and the index finger). Pressure is slowly applied to the device wherein the skin of one of the fingers enters the device and is pierced (punctured) by a stationary piercer. The slow pressure distracts the brain from pain. Also, the small size of the device reduces the anticipation of puncture pain. Since there are no moving parts, the device can be made extremely small, and is inexpensive to manufacture.

In accordance with an embodiment, a device for piercing the skin to obtain a blood sample includes a sleeve which has an open first end and a cavity. A piercer is disposed within the cavity of the sleeve, the piercer having a tip which is positioned near the open first end of the sleeve. When used to obtain the blood sample, the piercer is stationary and does not move with respect to the sleeve.

In accordance with another embodiment, the sleeve has a closed second end opposite the open first end. The piercer has a base which is fixedly connected to the closed second end of the sleeve.

In accordance with another embodiment, the sleeve has a central axis. The piercer is disposed along the central axis of the sleeve.

In accordance with another embodiment, the open first end of the sleeve includes a rim which defines a surface. The tip of the piercer is recessed from the surface.

In accordance with another embodiment, the tip is recessed about 0.25 mm from the surface.

In accordance with another embodiment, the sleeve has a central axis. The open first end of the sleeve includes a rim which defines a plane, the plane forms an acute angle with the central axis.

In accordance with another embodiment, the sleeve is circular and has a diameter of between about 5 mm and about 8 mm.

In accordance with another embodiment, the device has no moving parts.

Other embodiments, in addition to the embodiments enumerated above, will become apparent from the following detailed description, taken in conjunction with the accompanying drawings, which illustrate, by way of example, the principles of the device and method of use.

BRIEF DESCRIPTION OF THE DRAWINGS

FIG. 1 is top plan view of a device for piercing the skin to obtain a blood sample;
FIG. 2 is a side elevation view of the device;
FIG. 3 is a bottom plan view of the device;
FIG. 4 is a perspective view of the device;
FIG. 5 is a cross sectional view along the line 5-5 of FIG. 1;
FIG. 6 is a reduced perspective view of the device being used;
FIG. 7 is an enlarged cross sectional view along the line 7-7 of FIG. 6;
FIG. 8 is an enlarged view of a finger pad after use of the device;
FIG. 12 is a top plan view of a second embodiment of the device;
FIG. 13 is a side elevation view of the second embodiment device;
FIG. 14 is a bottom plan view of the second embodiment device;
FIG. 15 is a perspective view of the second embodiment device;
FIG. 16 is a cross sectional view along the line 16-16 of FIG. 12;
FIG. 17 is an end elevation view of the second embodiment device puncturing the skin of a finger;
FIG. 18 is a view of a finger pad after use of the second embodiment device; and,
FIG. 19 is a reduced perspective view of the hand of a user after the second embodiment device was used.

DETAILED DESCRIPTION OF THE INVENTION

Figure 9:
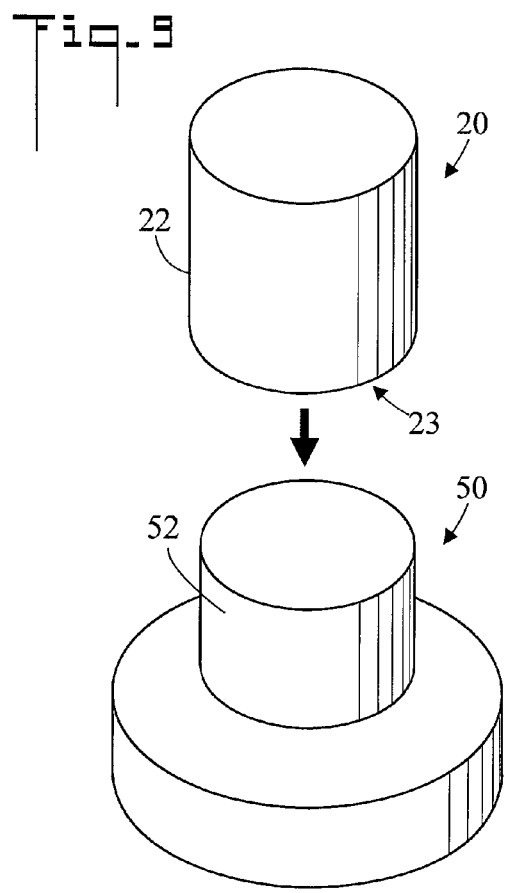
FIG. 9 is a perspective view of the device and a piercer bender.

Referring initially to FIGS. 1-5, there are illustrated top plan, side elevation, bottom plan, perspective, and cross sectional views respectively of a device for piercing the skin to obtain a blood sample, the device generally designated as 20. Device 20 includes a sleeve 22 which has an open first end 23 having a rim 24, and a cavity 26. In the shown embodiment, sleeve 22 is circular (cylindrical) and has a diameter D of between about 5 mm and about 8 mm, a length L of between about 5 mm and about 8 mm, and a wall thickness of about 0.5 mm. It may be appreciated however, that sleeve 22 could be other shapes such as oval or even rectangular. Sleeve 22 serves as a hood or sheath which protects a piercer (see discussion below). In an embodiment, sleeve 22 is made of a hard material such as a polymer (e.g. polypropylene), metal, hard rubber, or the like.

A single piercer 28 is disposed (invaginated) within cavity 26 of sleeve 22. Piercer 28 has a tip 30 which is positioned near the open first end of sleeve 22. As used herein the term "piercer" includes any sharp pointed member which can penetrate the skin of the user for the purpose of obtaining a blood sample (e.g a lancet, needle, or the like). In an embodiment, piercer 28 is fabricated from stainless steel. In an embodiment, piercer 28 has a gauge of 23, 28 or 33.

Referring in particular to FIG. 5, sleeve 22 also has a closed second end 32 opposite open first end 23. Piercer 28 has a base 34 which is fixedly connected to closed second end 32 of sleeve 22. Sleeve 22 also has a central axis 36, and piercer 28 is disposed along central axis 36 of sleeve 22. Rim 24 of the open first end 23, defines a surface S, which in the shown embodiment is a plane (shown on edge in FIG. 5). Tip 30 of piercer 28 is recessed a distance d from surface S. That is, tip 30 is slightly set back into cavity 26 so that the skin of the user must be forced by applied pressure into cavity 26 in order to obtain penetration by tip 30 (refer also to FIG. 7 and the associated discussion). In an embodiment tip 30 is recessed a distance d of about 0.25 mm from surface S.

An important feature of device 20 is that it has no moving parts. As such, when device 20 is used to obtain the blood sample, piercer 28 does not move with respect to sleeve 22.

FIG. 6 is a reduced perspective view of device 20 being used, and FIG. 7 is an enlarged cross sectional view along the line 7-7 of FIG. 6. Device 20 is held between two fingers of one hand so that the open first end of sleeve 22 abuts one of the two fingers. As used herein the term "finger" means any of the five digits of the hand. In the shown embodiment device 20 is held pincer fashion between the thumb 500 and the index finger 600, with the open first (piercing) end 23 of device 20 adjacent the index finger 600. It may be appreciated however, that device 20 could also be finger grasped between the thumb and any of the other fingers (i.e. the middle finger, the ring finger, or the little finger). The two fingers are used to apply pressure on both ends of device 20 (as shown by the opposing arrows), wherein the skin of the finger which abuts open first end 23 of sleeve 22 (index finger 600 as shown) enters cavity 26 and is pierced by piercer 28. As is shown in FIG. 7, the pressure (squeezing) is applied to device 20 by thumb 500 and index finger 600, wherein the tissue of index finger 600 enters cavity 26 and is pierced by tip 30 of piercer 28. It is noted that only tip 30 piercer 28 enters the flesh of the finger 600. And, grasping the device in between the pads of the fingers gives the user a feeling of containment and security.

In an embodiment, the pressure applied to device 20 is slow and between about 15 seconds and about 20 seconds in duration. The pressure is gradually increased until skin penetration is effected. This slow pressure mechanism results in less puncture pain, by replacing the sharp pain associated existing devices with a dull aching pain. Moreover, since device 20 is used by applying opposing finger pressure, it can be used with a single hand more efficiently than other devices currently on the market. Before pressure is applied, feeling rim (annulus) 24 (refer to FIG. 4) without the tip 30 of piercer 28 gives the user a feeling of comfort that the subsequent penetration piercing will not be deep. Only about one mm of tip 30 will penetrate the epidermis and part of the papillary dermis of the user, resulting in less pain. It is noted that, as finger pressure is increased, the depth of penetration of tip 30 will also increase. As such, with practice the user can learn to limit the pressure to just that required to obtain a blood sample, but not enough to pierce unnecessarily deep.

The piercing process using device 20 produces three different types of sensation; touch, dull aching pain, and sharp pricky pain. This type of mixed sensations distracts the brain from the sharp pricky pain. Large diameter nerve fibers (A-beta fibers) responsible for transmitting signals of touch to the brain, and have the ability to close the pain gate and block signals from other smaller diameter nerve fibers which transmit pain. This is explained by the gate control theory of pain which was put forward by Ronald Melzack and Patrick Wall in 1965 (British Medical Journal, 1978 Aug. 26; 2(6137): 586-587).

FIG. 8 is an enlarged view of a finger pad after use of device 20. If the proper pressure is applied, rim 24 (refer to FIG. 4) will leave an indentation 40 (circular as shown) on the skin. FIG. 8 also shows a drop of blood 800 which was obtained using device 20.

Referring now to FIG. 9, there is illustrated a perspective view of device 20 and a piercer bender 50, which combine to form a system. Piercer bender 50 is a tool which is shaped and dimensioned to be received by open first end 23 of sleeve 22, so that piercer bender 50 can be forced into cavity 26 of sleeve 22, contact tip 30 of piercer 28, and permanently bend piercer 28 (also refer to FIGS. 10 and 11). As a safety precaution to prevent the transmission of disease, after device 20 is used to obtain a sample of blood, piercer bender 50 is used to bend piercer 28 so that device 20 cannot be used again, and must be discarded.

Figure 10:
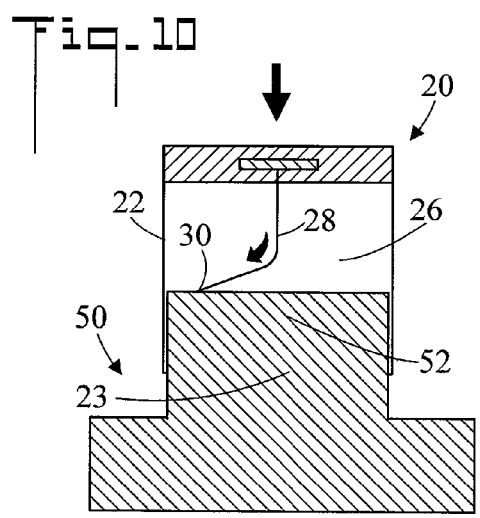
FIG. 10 is a cross sectional view of the piercer bender bending the piercer.
Figure 11:
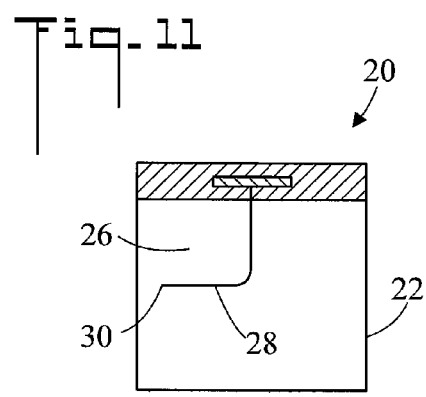
FIG. 11 is a cross sectional view of the device with the piercer bent.

FIG. 10 is a cross sectional view of the piercer bender 50 bending piercer 28. Open first end 23 of device 20 is placed over an upwardly projecting post 52 of piercer bender 50, post 52 being sized to closely be received by cavity 26 of device 20. Device 20 is then pushed down upon piercer bender 50 so that post 52 contacts and permanently bends (deforms) piercer 28 (refer to FIG. 11). FIG. 11 is a cross sectional view of device 20 showing sleeve 22, cavity 26, bent piercer 28, and tip 30. It is noted that in FIGS. 10 and 11, the narrow side of piercer 28 is shown, as opposed to the broad side shown in FIGS. 5 and 7.

FIGS. 12-16 are top plan, side elevation, bottom plan, perspective, and cross sectional views respectively of a second embodiment of the device generally designated as 120. This embodiment is similar to the embodiment of FIGS. 1-5, except that rim 124 is angled. That is, rim 124 of open end 123 of sleeve 122 defines a plane P, wherein plane P forms acute angle A with central axis 136. It is noted that in the previous embodiment of FIGS. 1-5, rim 24 is approximately perpendicular to central axis 36. Referring specifically to FIG. 16, it is noted that similar to FIG. 5, tip 130 of piercer 128 is recessed a distance d from plane P. FIG. 17 is an end elevation view of the second embodiment device 120 puncturing the skin of a finger 600, FIG. 18 is a view of a finger pad after use of the second embodiment device 120, and, FIG. 19 is a reduced perspective view of the hand of a user after the second embodiment device 120 was used. It is noted that second embodiment device 120 is positioned on the periphery of finger 600 where curvature starts. By putting piercer 28 in the periphery of the finger's pad the puncture is at an acute angle rather than perpendicular to the finger pad, and as such results in less pain and tissue resistance (the same mechanism as a mosquito's proboscis during penetration).

Testing Results

A comparative study was conducted to evaluate the pain scale for device 20 in comparison to old style lancet devices. 30 patients were enrolled in this study. A pain scale graded from 0 to 3 was created to measure the intensity of puncture pain, where; 0=no pain, 1=mild pain, 2=moderate pain, and 3=severe pain. The puncture pain induced by device 20 was compared to the old style lancet, according to the past memory of recent use by the test subjects. Conclusion: The average pain level from the old style lancet device was significantly higher than from device 20.

In terms of use, a method for a user to use two fingers of one hand to pierce the skin to obtain a blood sample includes: (refer to FIGS. 1-19)

(a) providing a device 20 for piercing the skin to obtain a blood sample, including;
    a sleeve 22 having an open first end 23 and a cavity 26;
    a piercer 28 disposed within cavity 26 of sleeve 22, piercer 28 having a tip 30 which is positioned near open end 23 of sleeve 22; and,
    when used to obtain the blood sample, piercer 28 not moving with respect to sleeve 22;
(b) holding device 20 between the two fingers 500 and 600 so that open first end 23 of sleeve 22 abuts one of the two fingers 600; and,
(c) using the two fingers 500 and 600 to apply pressure on device 600, wherein the skin of the finger 600 which abuts open first end 23 of sleeve 22 enters cavity 26 and is pierced by piercer 28.

The method further including:
in (c), the pressure being applied for between about 15 seconds and about 30 seconds.

The method further including:
in (c), the pressure being applied over a period of time having a start and a finish; and,
in (c), the pressure increasing from the start to the finish.

The method further including the two fingers including a thumb and one other finger;
in (c), using the thumb and the one other finger to apply pressure on the device.

The method further including:
after (c), observing that an indentation 40 is left on the finger 600 which abutted open first end 23 of sleeve 22.

The method further including:
providing a piercer bender 50 which is shaped and dimensioned to be received by open first end 23 of sleeve 22;
after (c), inserting piercer bender 50 into open first end 23 of sleeve 22 until piercer bender 50 contacts tip 50 of piercer 28; and,
forcing piercer bender 50 into cavity 26 of sleeve 22 so that piercer bender 50 permanently bends piercer 28.

The embodiments of the device method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the device and method should be construed as limiting the invention to a particular embodiment or combination of embodiments. The scope of the invention is defined by the appended claims.

I claim:

1. A system for piercing the skin to obtain a blood sample, the system cooperating with a finger and a thumb, the system comprising:
    a device for puncturing the skin to obtain the blood sample, including:
        a sleeve having an open first end, a central axis, and a cavity, said open first end defining a rim;
        a single piercer disposed within said cavity of said sleeve, said piercer having a tip which is positioned within said cavity at said open first end of said sleeve, said piercer having a broad side and a narrow side so that it can be bent and permanently deformed, said piercer disposed along said central axis of said sleeve;
        when used to obtain the blood sample the device is held between the thumb and the finger, and the skin must be forced into said cavity in order to be pierced by said piercer; and,
    a piercer bender which is shaped and dimensioned to be closely received by said open first end of said sleeve, so that said piercer bender can be forced into said cavity of said sleeve, contact said tip of said piercer, and bend and permanently deform said piercer.

2. A method for a user to use two fingers of one hand to pierce the skin to obtain a blood sample, the method comprising:
(a) providing a device for piercing the skin to obtain a blood sample, including:
    a sleeve having an open first end, a central axis, and a cavity, said open first end defining a rim;
    a single piercer disposed within said cavity of said sleeve, said piercer having a tip which is positioned within said cavity at said open first end of said sleeve, said piercer having a broad side and a narrow side so that it can be bent and permanently deformed, said piercer disposed along said central axis of said sleeve; and,
    when used to obtain the blood sample, said piercer not moving with respect to said sleeve;
(b) holding said device between the two fingers so that said open first end of said sleeve abuts one of the two fingers;
(c) using the two fingers to apply pressure on said device, wherein the skin of the finger which abuts said open first end of said sleeve enters said cavity and is pierced by said piercer;
(d) providing a piercer bender which is shaped and dimensioned to be closely received by said open first end of said sleeve, so that said piercer bender can be forced into said cavity of said sleeve, contact said tip of said piercer, and bend and permanently deform said piercer;
after (c), inserting said piercer bender into said open first end of said sleeve until said piercer bender contacts said tip of said piercer; and,
forcing said piercer bender into said cavity of said sleeve so that said piercer bender bends and permanently deforms said piercer.

3. The method of claim 2, further including:
in (c), said pressure being applied for between about 15 seconds and about 30 seconds.

4. The method of claim 3, further including:
in (c), said pressure being applied over a period of time having a start and a finish; and,
in (c), said pressure increasing from said start to said finish.

5. The method of claim 2, the two fingers including a thumb and one other finger, the method further including:
in (c), using the thumb and the one other finger to apply pressure on said device.

6. The method of claim 2, further including:
after (c), observing that an indentation is left on the finger which abutted said open first end of said sleeve.

\* \* \* \* \*